United States Patent [19]
Johnson

[11] Patent Number: 5,467,639
[45] Date of Patent: Nov. 21, 1995

[54] UNIVERSAL PENETRATION TEST APPARATUS AND METHOD

[75] Inventor: Phillip W. Johnson, Rochester, Minn.

[73] Assignee: Mayo Foundation for Medical Education and Research, Rochester, Minn.

[21] Appl. No.: 291,745

[22] Filed: Aug. 17, 1994

Related U.S. Application Data

[63] Continuation of Ser. No. 4,839, Jan. 19, 1993, abandoned.

[51] Int. Cl.⁶ .................................................. G01N 15/08
[52] U.S. Cl. ................................................................. 73/38
[58] Field of Search ........................... 73/38, 64.47, 818, 73/820, 821, 78, 81, 82, 84, 85

[56] References Cited

U.S. PATENT DOCUMENTS 1,232,782  7/1917  Field ........................................ 73/81

(List continued on next page.)

FOREIGN PATENT DOCUMENTS

| 1168469 | 6/1984 | Canada | 73/38 |
|---|---|---|---|
| 200941 | 11/1984 | Japan | 73/78 |
| 88350 | 5/1985 | Japan | 73/82 |
| 252232 | 10/1988 | Japan | 73/78 |

OTHER PUBLICATIONS

Final Report Elbow Lean Test, Protocol No. 900543-1, Lab No. 28873B, Nelson Lab., Inc. May 3, 1990.
Bernard Miller, Chapter IV, "Experimental Aspects Of Fiber Wetting And Liquid Movement Between Fibers", Textile Research Institute, Princeton, N.J. pp. 121–147.
Federal Register, vol. 56, No. 235, Friday, Dec. 6, 1991, Rules and Regulations, pp. 64124–64139.
Norman W. Henry, III, "Biological Resistant Clothing–Standards in the Making", *ASTM Standardization News*, May, 1992.
Brochure for F 903 Penetration Test Apparatus, Wilson Road Machine Shop 1170 Wilson Road, Rising Sun, Maryland 21911.
Standard Test Method For Resistance Of Protective Clothing Materials To Synthetic Blood, ASTM.
Final Report Elbow Lean oX174 Challenge Test Protocol No. 900543-1 Nelson Laboratories, Inc., Salt Lake City, Utah 84117.
K. W. Altman, et al., "Transmural surgical gown pressure measurements in the operating theater", American Journal of Infection control, vol. 19, No. 3, Jun. 1991, pp. 147–155.

*Primary Examiner*—Hezron E. Williams
*Assistant Examiner*—Daniel S. Larkin
*Attorney, Agent, or Firm*—Merchant, Gould, Smith, Edell, Welter Schmidt

[57] ABSTRACT

A portable test apparatus and method for measuring and comparing the resistance of protective clothing materials, and other materials, to penetration by liquids, pathogens, and fluid transmissible particles. The test apparatus employs weights with center holes, which fit over an elongated weight support assembly which is held upright in a frame. To perform the test, a highly resilient and absorbent sponge is placed in a small tray and soaked with a test fluid, the test material is then placed over the sponge, a piece of absorbent paper is placed over the test material, the frame is centered above the test material, the elongated weight support assembly is placed through the center hole of the frame until the flat surface of the weight support assembly is in contact with the absorbent paper, and weights are placed onto the elongated weight support assembly. When the full pressure of single or multiple weights and elongated weight support assembly are on the test material, the test begins. Pass/failure is determined by observing the test material through the end of the transparent rod. If the fluid appears under the support member tip within a predetermined period of time, e.g., five minutes, the material fails at the weight applied. If no fluid appears, the test is repeated, with additional weights, until the material fails. After repeated samplings, the failure threshold is determined and the material's fluid pressure resistance is recorded.

3 Claims, 5 Drawing Sheets

U.S. PATENT DOCUMENTS

| | | | |
|---|---|---|---|
| 2,078,296 | 4/1937 | Vadner | 73/821 |
| 3,443,423 | 5/1969 | Lou Ma | 73/821 |
| 3,504,527 | 4/1970 | Marshall | 73/38 |
| 3,577,767 | 5/1971 | Stedile | 73/38 |
| 4,050,995 | 9/1977 | Bredeweg | 204/1 T |
| 4,194,041 | 3/1980 | Gore et al. | 428/315 |
| 4,214,320 | 7/1980 | Belkin | 2/114 |
| 4,310,057 | 1/1982 | Brame | 73/864.74 |
| 4,327,731 | 5/1982 | Powell | 128/287 |
| 4,344,999 | 8/1982 | Gohlke | 428/212 |
| 4,382,990 | 5/1983 | Coates | 428/290 |
| 4,385,517 | 5/1983 | Sorce et al. | 73/38 |
| 4,448,204 | 5/1984 | Lichtenstein | 128/736 |
| 4,454,055 | 6/1984 | Richman et al. | 252/194 |
| 4,495,795 | 1/1985 | Gupta | 73/38 |
| 4,565,089 | 1/1986 | Arciszewski et al. | 73/85 |
| 4,678,757 | 7/1987 | Rapkin et al. | 436/169 |
| 4,747,685 | 5/1988 | Suzuki | 356/36 |
| 4,896,418 | 1/1990 | Yearsley | 29/827 |
| 4,918,981 | 4/1990 | Gore | 73/76 |
| 4,948,561 | 8/1990 | Hinckley et al. | 422/61 |
| 4,961,339 | 10/1990 | Kleis et al. . | |
| 5,216,727 | 6/1993 | Vakshoori et al. . | |
| 5,265,177 | 11/1993 | Cho et al. . | |

UNIVERSAL PENETRATION TEST APPARATUS AND METHOD

This is a continuation of application Ser. No. 08/004,839, filed Jan. 19, 1993, now abandoned.

FIELD OF THE INVENTION

The present invention relates to test apparatus and methods for measuring the resistance of materials; e.g., protective fabrics, to penetration by fluids, pathogens and other fluid/fluid vapor transmissible particles.

BACKGROUND OF THE INVENTION

The permeability of a material relates to the ability of a fluid and fluid transmissible particles to penetrate the material. Different materials have different permeabilities. Some materials are impervious to some fluids, that is, they are unable to be penetrated by those fluids. Some materials are pervious to various fluids. Of course, most materials are semi-impervious to various fluids.

In an effort to protect workers who are exposed to bloodborne pathogens or other infectious materials at work, the Occupational Safety and Health Agency (OSHA) has set requirements for the penetrability of protective clothing by bloodborne pathogens and/or other infectious materials; e.g., the Bloodborne Pathogen Standard of Dec. 6, 1991.

To determine the permeability of various materials, researchers have been trying to find a simple, universal test method and apparatus. One simple pass/fail penetration test is referred to as the Elbow Lean Test. In this test, a conventional rubber stamp ink pad is saturated with a challenge fluid; that is, the fluid with which the permeability of a particular material is to be tested. The test material is then placed over the pad with the outside down against and in contact with the stamp pad. A person then leans on the pad with their elbow. If fluid is detected on the inside surface of the material, the material fails the test. If no fluid is detected, the material passes the test. This is a very general pass/fail test as the force exerted by one's elbow may vary greatly; e.g., twenty to seventy pounds.

Recently, there has been substantial concern over the safety of healthcare professions and others who come in contact with blood that may contain pathogens such as hepatitis B virus (HBV) and human immunodeficiency virus (HIV), as well as other infectious materials.

In some penetration tests, the permeability of various pathogens or other fluid transmitted particles is being tested. In these cases, alternative detection means other than visual detection is used to determine if penetration has occurred. For example, chemical detectors, radioactive detectors, etc. might be used. In many cases alternative detectors are used where the fluid is colorless and cannot be visually detected. If the fluid is colorless, dyes or other coloring agents can be added to aid in the visual detection process.

Material penetration testing is replete with testers which use pressurized or impact fluid penetration mechanisms to demonstrate material liquid penetration resistance. These tests and testers include the following: INDA Water Spray Test IST 80.1-70 (R82), INDA Impact Penetration Test IST 80.5-70 (R82), INDA Hydro Pressure Test IST 80.6-70 (R82), INDA Saline Repellency Test IST 80.7-70 (R82), AATCC Water Resistance: Suter Hydrostatic Pressure Test 127-1985, AATCC Spray Rating Test 22-1985, ATTCC Rain Test 35-1985, Federal Gov. Water Resistance of Coated Cloth; High Range, Hydrostatic Pressure Method, ASTM Mullen Hydrostatic test D751, ASTM Standard Test Method For Resistance of Protective Clothing To Penetration By Liquids F903-90, ASTM Emergency Standard Test Method For Resistance Of Protective Clothing Materials To Synthetic Blood F23.40.01, and ASTM Emergency Standard Test Method For Resistance Of Protective Clothing Materials To Penetration By Bloodborne Pathogens Using Viral Penetration As A Test System F23.40.02.

The testers used in these tests are typically complicated in design, cumbersome to set up, time consuming to use, difficult to clean, semi-portable, not suitable for field use, expensive, and based on subjecting test materials to contained hydrostatic pressures which are not representative of actual use conditions experienced by wearers of protective clothing where free flowing fluids on the outer surfaces of a material are momentarily pressurized against the clothing and skin of the wearer by fingers, elbows, and other objects. A good example of this type of testing is American Society for Testing and Materials (ASTA) F 903-90 standard test method for resistance of protective clothing materials to penetration by liquids. This test requires that the material to be tested is mounted in a test cell which in turn is attached to an air pressure line. The challenge fluid is then exposed to a predetermined air pressure for a predetermined period of time.

The contained hydrostatic pressure methods also unnaturally expand, stretch, and pull apart the material structure thereby causing failure of the liquid/pathogen barrier and avoidable negative results in both visible liquid and pathogen penetration tests. Therefore, the contained hydrostatic pressure method is too rigorous for 90% of the protective products market and unnecessarily expensive for manufacturers and consumers.

The present invention solves many of the problems associated with the prior art.

SUMMARY OF THE INVENTION

The present invention relates to an apparatus and method for testing the penetration of sheet material by fluids and fluid transmitted particles and pathogens.

Throughout this description reference will be made to fluid penetration of the test material. This will refer to both the fluid itself and/or particles/pathogens contained therein which are often referred to as the challenge substance. The use of the term fluid refers to both gas/vapor and liquid substances.

One embodiment of the invention provides a universal penetration test apparatus of simple and inexpensive design and which is simple to set up and easy to use.

One embodiment of the invention provides a universal penetration test apparatus which accurately defines the range of pressures that a test material will withstand, before penetration, by a test fluid.

One embodiment of the invention provides universal penetration test apparatus and methods which can be used in a minimum amount of time.

One embodiment of the invention provides universal penetration test apparatus which is easily cleaned after use.

One embodiment of the invention provides a universal penetration test apparatus which is small and highly portable.

One embodiment of the invention provides universal penetration test apparatus and methods which are suitable for laboratory and field use by both technical and non-technical individuals.

One embodiment of the invention provides universal penetration test apparatus which can be used to test most types of materials to penetration by fluids. One embodiment is particularly suited for testing penetration of bloodborne pathogens.

One embodiment of the invention provides universal penetration test apparatus which can be used for testing any type of material which is designed to prevent the penetration of fluids.

One embodiment of the invention provides universal penetration test apparatus which simulates actual use conditions by applying non-contained hydrostatic and mechanical pressures to the surface of a test material.

One embodiment of the invention provides universal penetration test apparatus which causes minimal deflection, expansion, stretching, or pulling apart of the test material structure.

One embodiment of the invention provides universal penetration test apparatus which allows easy viewing of the surface area being tested.

One embodiment of the invention provides universal penetration test apparatus which uses a minimal amount of weight in proportion to the surface area of the apparatus contact point to achieve failure of the test material.

One embodiment of the invention traps, contains and creates hydrostatic pressure without external air or liquid supply lines.

In one embodiment, a universal penetration test apparatus includes a dense latex foam pad with the challenge fluid to prevent the challenge fluid from moving rapidly and perpendicularly/radially away from the pressure point before the challenge fluid penetrates the test material. In other words, the path of least resistance is through the test material.

In one embodiment, a universal penetration test apparatus comprises a tray containing the fluid saturated latex foam pad so as to prevent loss of the fluid from the test site.

In one embodiment the present invention comprises a universal material penetration tester kit including (1) a plurality of weights in varying sizes with center holes, (2) a hollow sleeve, preferably made of metal or plastic, insertable into the center holes of the weights and having a protruding flange on its outer surface to support the weights, (3) a solid rod of clear material such as Plexiglass with a protruding flange near its base to support the sleeve, and with a rubber O-ring just above the flange to prevent the sleeve and rod from separating, (4) a collapsible frame with a center hole to support the rod and sleeve in an upright position, (5) a highly absorbent material, such as a sponge of dense latex foam or similar material, to contain a fluid or other substance often referred to as a challenge fluid or substance, and (6) a leak proof tray to hold the sponge.

In one embodiment of the invention an optional absorbent paper is used with a plastic coating on one side to protect the base of the rod from contamination by the challenge fluid or other substance in the sponge.

One embodiment of the invention provides a tester apparatus which eliminates the need for the frame, rod and sleeve member.

One embodiment of a test method in accordance with the principles of the present invention includes the following steps:

the sponge is placed in the tray, a challenge fluid or other challenge substance is applied to the sponge until it is saturated, a test material is placed with its outer surface down against the sponge, a piece of absorbent paper larger than the base of the plastic rod is placed on top of the test material with the absorbent side against the test material, the frame is opened and centered over the sample, the sleeve is placed down over the rod until it contacts the flange at the end of the rod and is locked in place by the pressure of the O-ring on the rod, and the rod/sleeve assembly is placed through the frame supporting hole until the rod base rests upon the paper. A weight is then placed down onto the sleeve until it contacts the sleeve flange. The test dynamics can be viewed through the end of the transparent rod. If the challenge fluid or other challenge substance does not penetrate the sample, additional weights are added until failure occurs, which is evident by the appearance of the challenge fluid or challenge substance on the absorbent paper as seen through the upper end of the rod.

Appearance of the challenge fluid or challenge substance in the absorbent paper under the rod base constitutes a failure of the test material at a specific pressure, e.g., pounds per square inch. The applied weight, on the test material is then determined by dividing the amount of the total weight resting on the test material by the surface area of the rod base. Therefore, by increasing or decreasing the weight and the diameter of the rod base in contact with the test material, more or less pressure can be applied to the test material. This qualitative analysis of samples can be used for selecting materials which can withstand penetration of specific fluids and other substances at the greatest pressure, and, as a product quality assurance tool.

In one embodiment, the rod base has a surface area of one square inch such that the pressure in pounds per square inch can be determined by simply determining the total weight in pounds. Likewise, other embodiments of the invention might be similarly sized for other units of measurement and/or sized so as to allow simple calculation of the pressure by the use of whole number factors.

Another embodiment of the invention comprises using a challenge fluid or challenge substance which may penetrate the sample without visible evidence. Confirmation of penetration can then be determined using standard laboratory procedures. For example, chemical detectors, radioactive detectors, etc. might be used. The fluid might also be colored with a suitable dye or colorant.

Yet another embodiment of the invention comprises weighing the absorbent paper before and after testing two different samples to determine which sample allowed the least amount of challenge liquid or material to pass through.

Control of fluid dynamics is also very important in obtaining valid results. If the test apparatus and methods are used without a sponge of the right density and thickness, the challenge fluid will move horizontally away from the pressure point at a velocity which is directly proportionate to the weight applied and the speed with which the weight is applied. The density and thickness of the sponge, in one embodiment, is selected to keep the challenge liquid (synthetic blood) under the sample long enough for the weight bearing rod to create a hydrostatic pressure between the liquid and the test material.

Another embodiment of the present invention includes a rod base having concentric circles of varying widths cut at different depths and at different distances apart with the inner most concentricity having the greatest depth; all of which combined, however, do not equal the combined thickness of the sponge, test material and paper. The effect of the concentric rings is to force the liquid toward the center which has the lowest pressure until the final peak pressure is applied by the weight bearing rod.

Another embodiment of the present invention includes a rod with a threaded end which screws into a base which serves as both the contact surface against the test material and as the support for the weights which slide down over the rod and rest against the upper surface of the base, thereby eliminating the need for the sleeve and the supporting frame.

Another embodiment of the present invention includes conical free-standing weights of different sizes with the top and bottom of each weight serving as a contact surface against the test material, thereby eliminating the sleeve and allowing for greater variations in applied pressures.

Another embodiment of the present invention includes spherical weights of different sizes. This embodiment eliminates the need for the rod, shaft and stand, but prevents viewing the test in progress.

These and various other advantages and features of novelty which characterize the invention are pointed out with particularity in the claims annexed hereto and forming a part hereof. However, for a better understanding of the invention, its advantages, and objects obtained by its use, reference should be had to the drawing which forms a further part hereof, and to the accompanying descriptive matter, in which there is illustrated and described a preferred embodiment of the invention.

BRIEF DESCRIPTION OF THE DRAWINGS

In the drawings, in which like reference numerals and letters generally indicate corresponding parts throughout the several views.

DETAILED DESCRIPTION OF AN EMBODIMENT OF THE INVENTION

Figure 1:
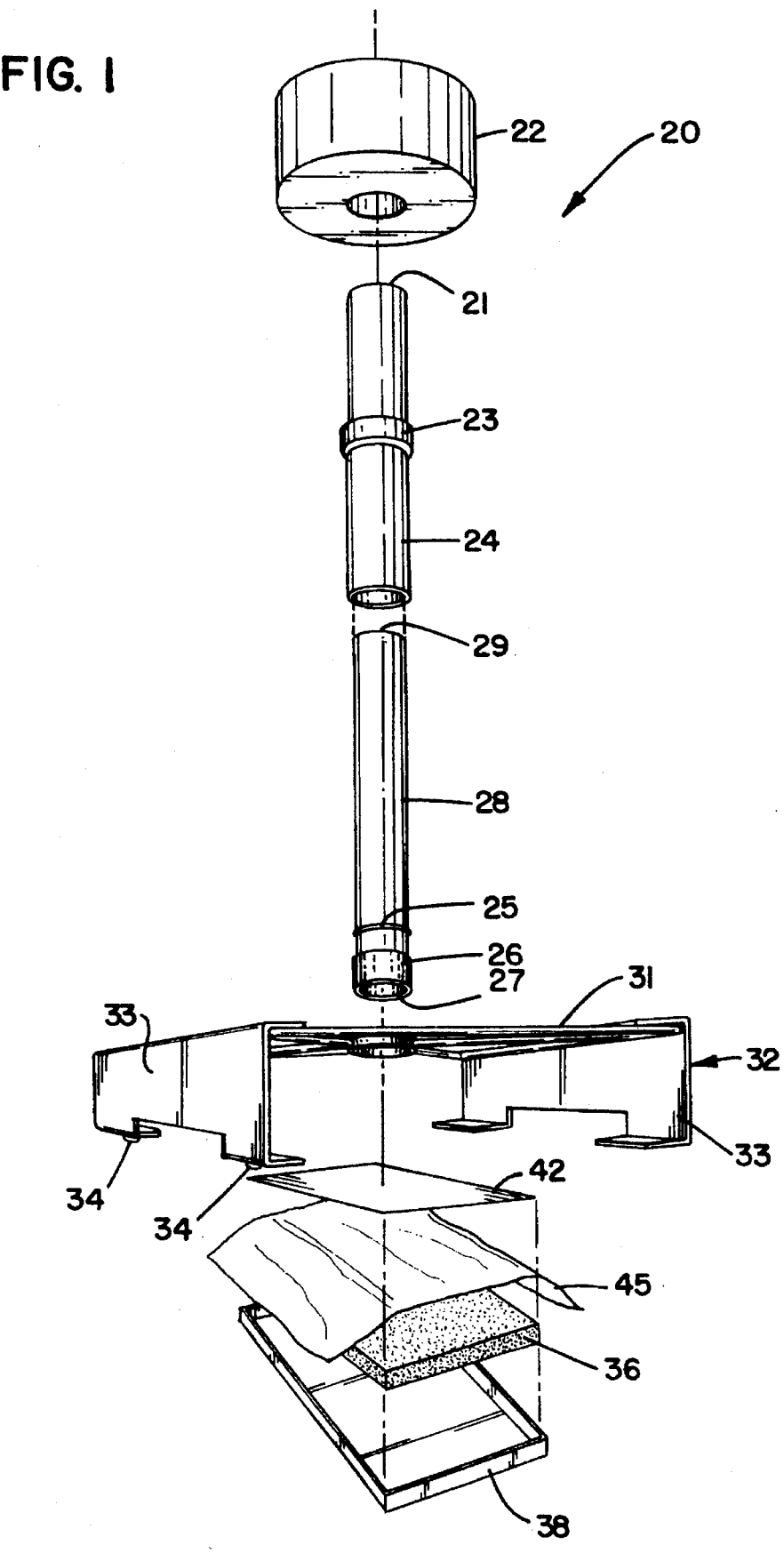
FIG. 1 is an exploded view of an embodiment of a universal penetration test apparatus generally in accordance with the principles of the present invention.
Figure 2:
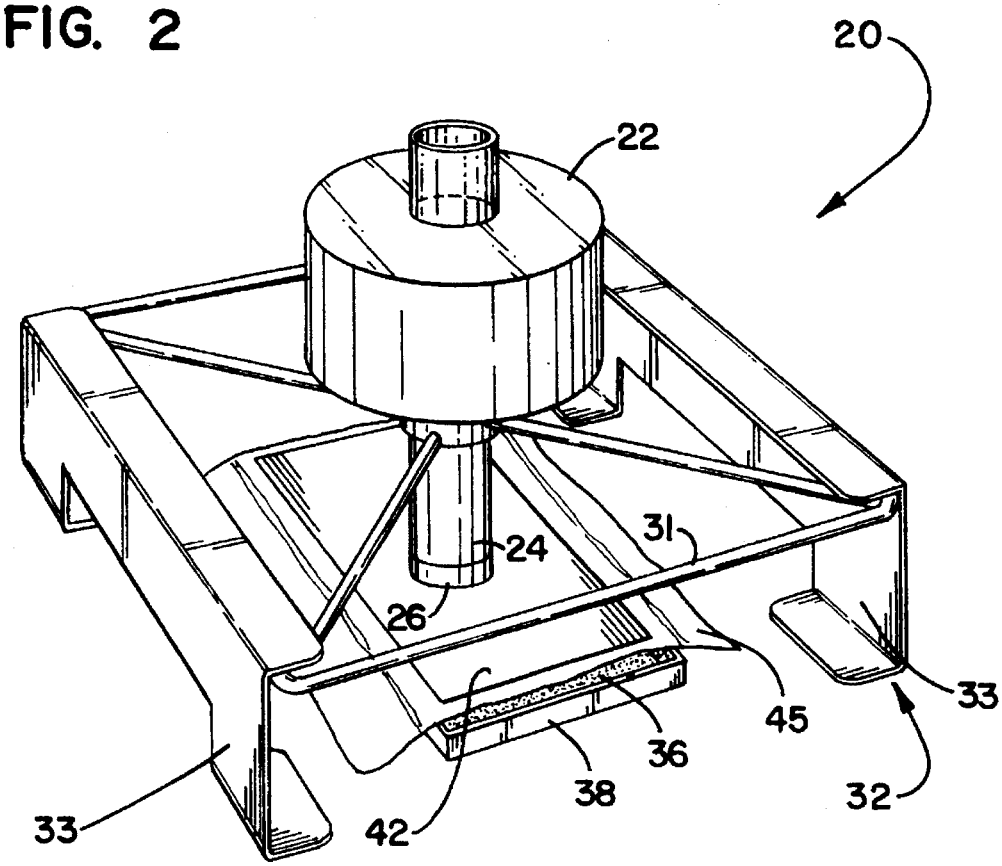
FIG. 2 is a view of the universal penetration test apparatus shown in FIG. 1, in its testing position.

Referring to FIGS. 1 and 2, there is shown an embodiment of a universal material penetration tester, designated by the reference numeral 20, generally in accordance with the principles of the present invention.

The embodiment shown in FIGS. 1 and 2 illustrates a universal material penetration tester 20, including a hollow sleeve 24, preferably made of metal or plastic. The sleeve 24 includes a top end 21. In addition, the sleeve 24, as shown, includes a flange 23 proximate the mid portion of the sleeve 24. A weight 22 is shown disposed for slidable insertion onto the end of the sleeve 24. Although not shown, a plurality of weights 22 might be place on the sleeve 24. The flange 23 supports the weight 22 on the sleeve. It will be appreciated that the flange might be integral to the sleeve or suitably positioned thereon by use of suitable attachment mechanisms such as threaded thumb screws or the like. A rod 28 of clear material such as plexiglass is slidably insertable into the sleeve 24. The rod 28 is shown as including a protruding flange 26 proximate its base end 27 for supporting the sleeve 24. An O-ring 25 disposed above the flange 26 assists in preventing the sleeve 24 and the rod 28 from separating. The sleeve 24 and rod 28 are slidably received in a collapsible frame assembly 32 having a center hole therein for assisting in supporting the rod 28 and sleeve 24 in an upright position. In the embodiment shown, the ends 21 and 29 of the sleeve and the rod, respectively, are substantially at the same height when the sleeve 24 is slid onto the rod 28. In some embodiments a plurality of sleeves and rods of various sizes might be provided with the tester apparatus.

The frame assembly 32 includes two U-shaped side members 33 and foot rests 34 protruding from the bottom of each of the U-shaped side members 33. A flat support member 31, having the hole disposed in the center thereof, interconnects the upper edges of the U-shaped side members 33. It will be appreciated that the frame assembly might take on any number of varying configurations and yet be in keeping with the principles of the invention. For example, to facilitate portability of the device, the frame assembly 32 might be collapsible and/or foldable onto itself.

Disposed in the frame assembly below the support member 31 is a highly absorbent material such as a sponge 36 of high density latex foam or similar material and a leak proof tray 38 for holding the sponge 36. The material 45 to be tested is shown disposed over the sponge 36. In this embodiment, an absorbent paper 42 such as a white absorbent laboratory paper with a plastic coating on a side facing the rod 28 is used to protect the base end 27 of the rod 28 from contamination by a challenge fluid or challenge substance which is contained in the sponge 36. It will be appreciated that the collapsible frame assembly and the sponge 36, the tray 38, the test material 45, and the absorbent paper 42, are supported by a suitable support surface such as a table top or the like not shown in the illustration.

Figure 3:
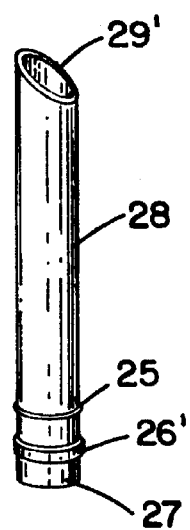
FIG. 3 is an alternate embodiment of the rod used in FIG. 1.
Figure 4:
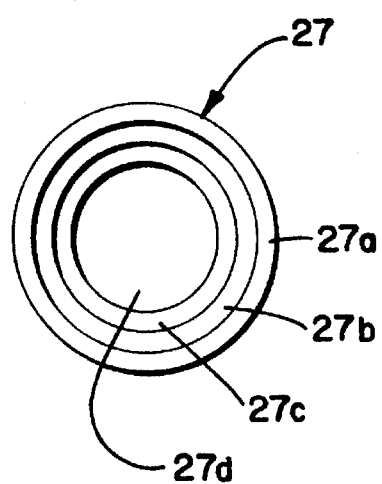
FIG. 4 is an end view of yet another alternate embodiment of the rod used in FIG. 1.

It will be appreciated that the various components of the embodiment illustrated in FIG. 1 might take on various alternative configurations and yet be in keeping with the principles of the invention. For example, as shown in FIG. 3 the rod 28 might have a flange 26' which does not extend all of the way to the base end 27. In addition, a top end 29' of the solid, transparent rod 28 is inclined at a 45 degree angle to facilitate viewing of the test material 45. In this embodiment, the end 29' of the rod 28 will preferably extend beyond the end 21 of the sleeve. As further illustrated in FIG. 4, the rod 28 might have concentric circles 27a–d, of varying widths, cut at different depths and at different distances apart, with the innermost concentrical circle or center of the rod having the greatest depth. All of the concentric circles combined, however, do not equal the combined thickness of the sponge, test material and absorbent paper. In some embodiments of the invention, the absorbent paper 42 might not be used. Moreover, variations on the sponge 36/tray 38 might be used. These are but a few of the many examples of variations which might be made in the various components of the universal material penetration tester 20.

One method of testing, using the above-described embodiment, as shown in FIG. 1, includes placing the sponge 36 in the leak proof tray 38. A challenge fluid or other challenge substance is then applied to the sponge 36 until it is saturated. The test material 45 is then placed on the sponge 36, with its outer surface abutting the sponge 36. A piece of the absorbent paper 42, larger than the base end 27 of the rod 28, is placed on top of the test material 45 with the absorbent side against the test material 45. The plastic coating of the absorbent paper 42 is facing the rod 28. The frame assembly 32 is suitably placed over the assemblage of the plastic tray 38, the sponge 36, the test material 45, and the absorbent paper 42. The sleeve 24 is inserted over the rod 28 until it contacts the flange 26 proximate the end of the rod 28 and is retained in place by the force of the O-ring 25 on the rod 28. The sleeve 24 and rod 28 assembly is placed through the hole in the frame support member 31 until the base end 27 of the rod 28 rests on the absorbent paper 42. A weight 22 is then placed down onto the sleeve 24 until it contacts the sleeve flange 23 and is supported thereby. The user then views through a viewing end of the rod 28. If, within a predetermined period of time, e.g., five minutes, the challenge fluid or other challenge material does not penetrate the test material so as to be absorbed by the absorbent paper 42, additional weights are added until failure occurs, which is evident by the appearance of the challenge fluid or challenge material on the absorbent paper, as seen through the viewing end 29 of the rod 28.

In one embodiment, the test apparatus 20 will include a plurality of weights 22 with at least some of the weights 22 having a different weight. In one embodiment, one-half, one, two, three, four and five pound weights 22 might be included. If used with a rod having a base end of one square inch, and a weight with the sleeve of one-half pound, this would allow measurements of up to sixteen pounds if all the weights were placed on the sleeve. If used with a rod having a base end of ¼ square inch, this would allow measurement up to sixty-four pounds. Up to one hundred twenty-eight pounds might be measured if a rod base end of ⅛ square inch were used. Of course, as opposed to using a smaller base end area, heavier weights might also be used.

Illustrated below is a weight/PSI conversion table with two different rod sizes; a first having a diameter of 1.128" or an area of 1" and a second having a diameter of 0.564" or an area of ¼".

| Applied Weight (lbs) | Rod #1 PSI | Rod #2 PSI | Applied Weight (lbs) | Rod #1 PSI | Rod #2 PSI |
|---|---|---|---|---|---|
| 1/16 | .0625 | .25 | 12.0 | 12.0 | 48.0 |
| 1/8 | .125 | .5 | 13.0 | 13.0 | 52.0 |
| 1/4 | .25 | 1.0 | 14.0 | 14.0 | 56.0 |
| 1/2 | .5 | 2.0 | 15.0 | 15.0 | 60.0 |
| 1.0 | 1.0 | 4.0 | 16.0 | 16.0 | 64.0 |
| 2.0 | 2.0 | 8.0 | 17.0 | 17.0 | 68.0 |
| 3.0 | 3.0 | 12.0 | 18.0 | 18.0 | 72.0 |
| 4.0 | 4.0 | 16.0 | 19.0 | 19.0 | 76.0 |
| 5.0 | 5.0 | 20.0 | 20.0 | 20.0 | 80.0 |
| 6.0 | 6.0 | 24.0 | 21.0 | 21.0 | 84.0 |
| 7.0 | 7.0 | 28.0 | 22.0 | 22.0 | 88.0 |
| 8.0 | 8.0 | 32.0 | 23.0 | 23.0 | 92.0 |
| 9.0 | 9.0 | 36.0 | 24.0 | 24.0 | 96.0 |
| 10.0 | 10.0 | 40.0 | 25.0 | 25.0 | 100.0 |
| 11.0 | 11.0 | 44.0 | 26.0 | 26.0 | 104.0 |

Legend: Rod Tip  #1   #2
        Diameter 1.128" .564"
        Area     1.00"  .25"

The weights might have differing lengths to reflect their different weight. In some embodiments, the collection of weights might include two or more weights 22 having the same weight, as well as weights 22 having different weights. In order to increase the total weight, additional weights 22 might be added onto the sleeve or the existing weight 22 might be replaced with one or more weights 22. In the embodiment shown, the weights 22 have a cylindrical shape, although other shapes might be used. In one embodiment, the rod base end 27 might have an area of one square inch and the weights have a diameter of four to six inches. The diameter of the weights ideally will not be too great so that the user can view the base end 27 of the rod 28 to make sure it is aligned properly with the surface of the absorbent paper 42. The weights might all have the same diameter or differ in diameter depending on their weight. In one embodiment the rod and sleeve might have a total weight of one-half pound.

Appearance of the challenge fluid or challenge material on the inner surface of the test material 45 under the rod 28 constitutes a failure of the test material 45 to a specific pressure. Such pressure might be measured in pounds per square inch, kg/cm2, kpa, etc. The applied weight, on the sample is then determined by dividing the amount of weight resting on the absorbent material 42 by the surface area of the rod base. Therefore, by increasing or decreasing the weight and the diameter of the rod base 27, in resting on the test material 24, more or less pressure can be applied to the test material's surface.

This qualitative analysis of samples can be used for selecting materials which can withstand penetration of specific challenge fluids and challenge substances such as blood, bloodborne pathogens at the greatest pressure, and as a product quality assurance tool. One of the many uses for such materials is in the design of protective clothing, such as gloves, arm shields, aprons, gowns, suits, hats, boots, masks and similar items which can limit human exposure to hazardous and biological liquids.

Another qualitative method consists of using a challenge fluid containing a pathogen which may penetrate the sample without visible evidence. Confirmation of pathogen penetration can then be determined using standard laboratory procedures.

Yet another quantitative method can also be used by weighing the absorbent paper before and after testing two different test materials to determine which test material allowed the least amount of challenge fluid or material to pass through.

Control of fluid dynamics is also very important in obtaining valid results. If the test apparatus and methods are used without a sponge of the right density and thickness, the challenge fluid will move horizontally away from the pressure point at a velocity which is directly proportional to the weight applied and the speed with which the weight is applied. The density and thickness of the sponge should be selected to keep the challenge fluid under the base end of the rod long enough for the weight bearing rod to create a hydrostatic pressure between the fluid and the test material. The ideal sponge will not allow any movement of fluid away from the rod base end. In one embodiment, a latex foam sponge 0.135 inch thick made by Shearing-Plough for foot and shoe padding is used. Foam sponge selection depends upon the surface tension of the challenge liquid. Liquids which have higher surface tensions and viscosities move slower and, therefore, require lower density foam sponge.

To increase this hydrostatic affect, the embodiment shown in FIG. 3 might be used wherein the rod base 27 has concentric circles of varying widths cut at different depths and at different distances apart with the inner most concentricity having the greatest depth. All of the concentric circles combined, however, do not equal the combined thickness of the sponge, test material, and paper. The effect of these concentric circles is to force the liquid toward the center which has the lowest pressure until the final peak pressure is applied by the weight bearing rod.

Figure 5:
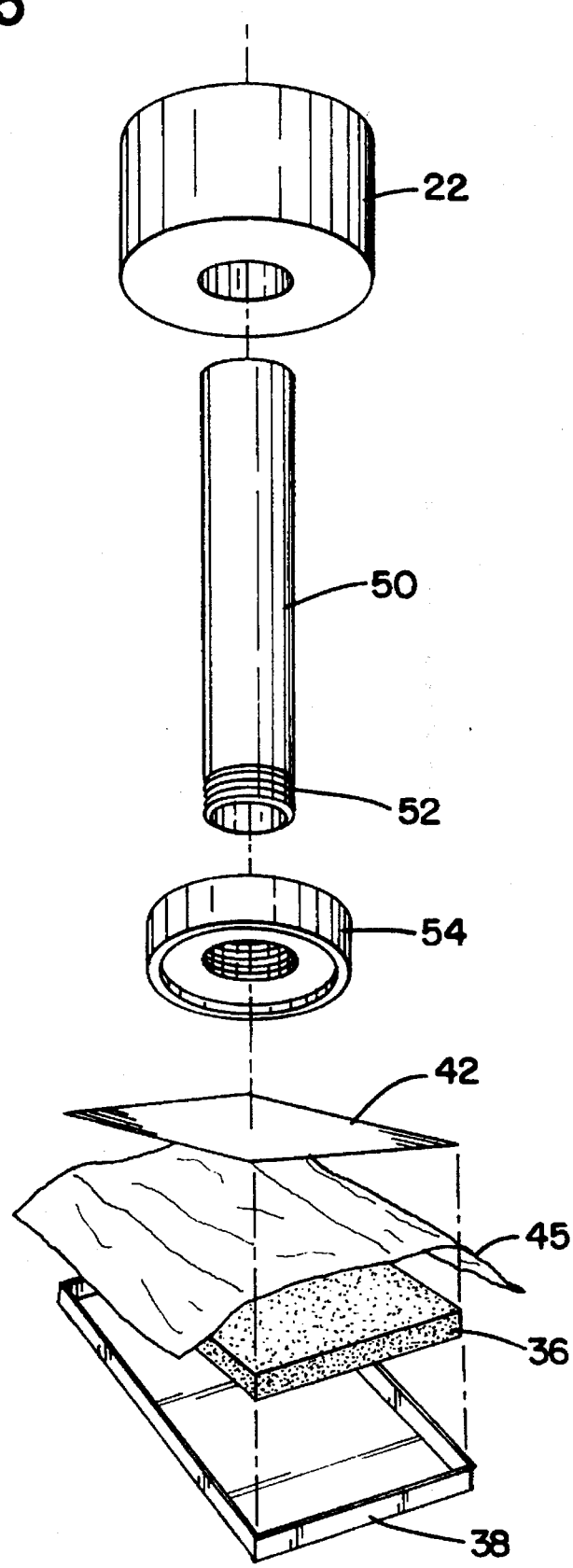
FIG. 5 is an exploded view of an alternate embodiment of a universal penetration test apparatus.
Figure 6:
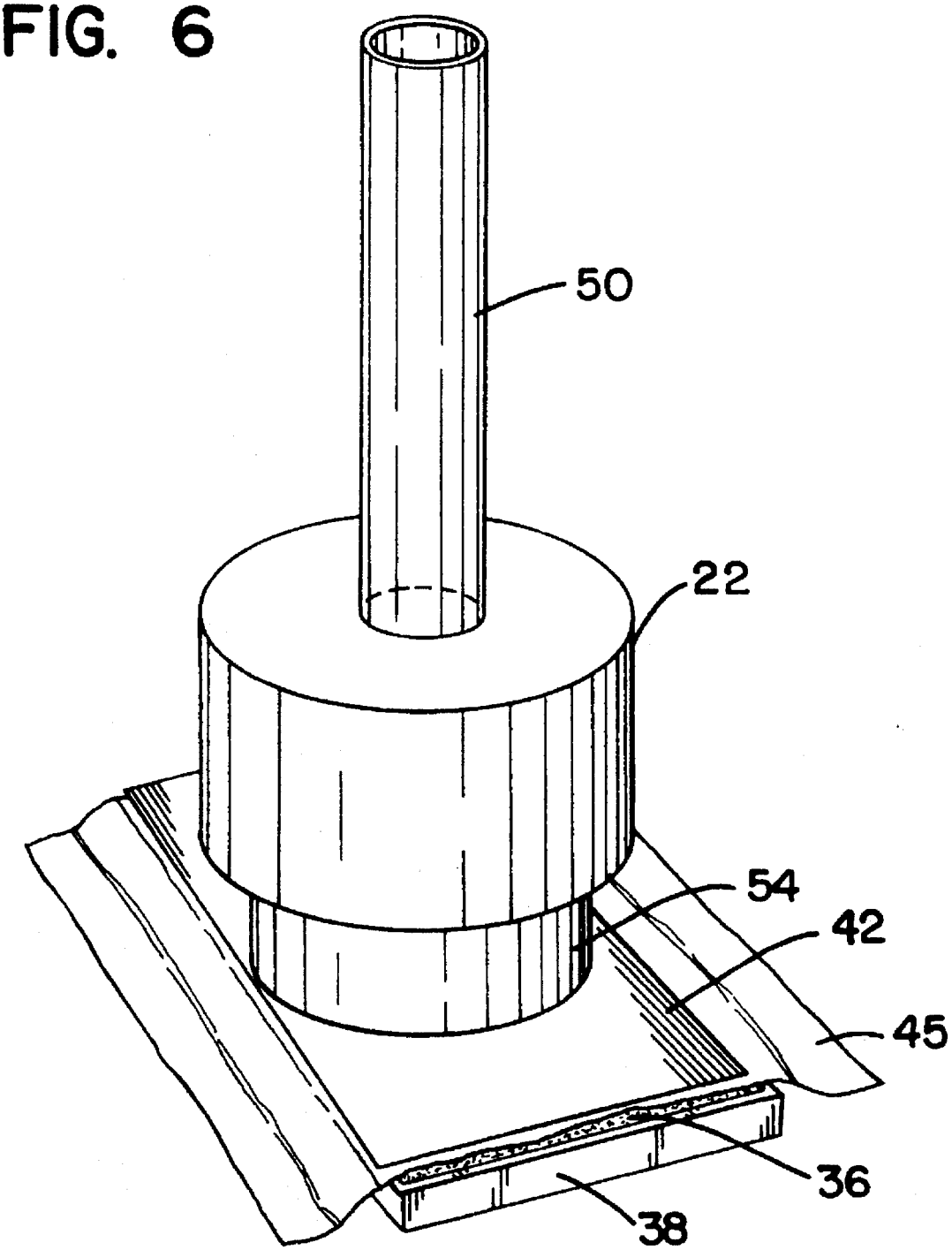
FIG. 6 is a view of the universal penetration test apparatus shown in FIG. 5, in its testing position.

In yet another embodiment of the present invention, as shown in FIGS. 5 and 6, a rod 50 might be used with a threaded end 52 which screws into a base 54 which serves as both the contact surface against the test material 45 and as the support for the weights 22 which slide down over the rod 50 and rest against the upper surface of the base, thereby eliminating the need for the sleeve and the supporting frame assembly 32. The base of the rod 50 in this embodiment can also include the concentric ring feature.

Figure 7:
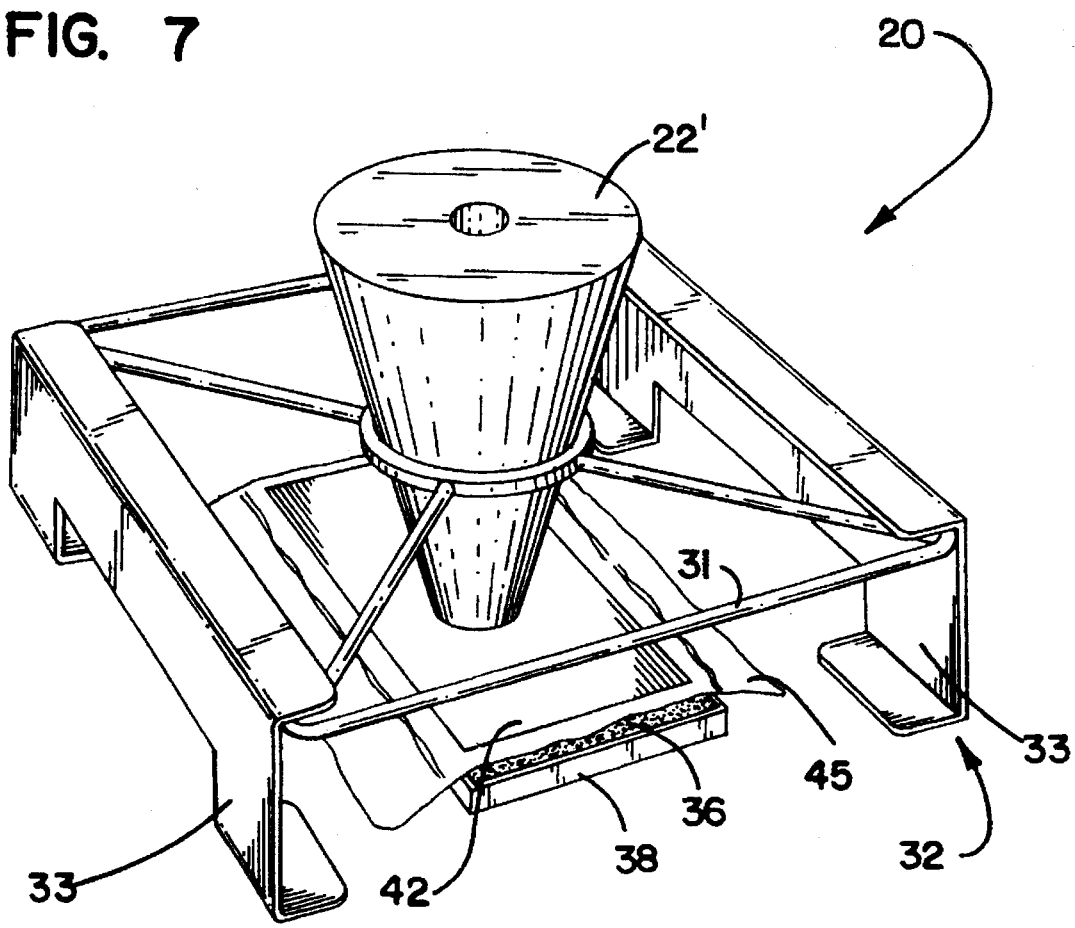
FIG. 7 is a perspective view of an alternate embodiment of the universal penetration test apparatus.

Yet another embodiment of the present invention, as shown in FIG. 7, comprises conical weights of different sizes with the top and bottom of each weight capable of serving as a contact surface against the test material 45, thereby eliminating the sleeve and the rod, and allowing for greater variations in applied pressures, simply by switching the weight end-for-end. However, this embodiment prevents viewing the test in progress. The weights must be removed to check the penetration. This embodiment can also include the concentric ring features.

Yet another embodiment of the present invention includes the use of spherical weights of different sizes. This embodiment eliminates the need for the rod, shaft, and stand, but prevents viewing the test in progress. The weights must be removed to see if the test material has been penetrated.

Ideally the components of the tester device are sterilizable by conventional means such as gas or chemicals.

It is to be understood, however, that even though numerous characteristics and advantages of the present invention have been set forth in the foregoing description, together with details of the structure and function of the invention, the disclosure is illustrative only, and changes may be made, in detail, especially in matters of shape, size and arrangement of parts within the principles of the invention, to the full extent indicated by the broad general meaning of the terms in which the appended claims are expressed.

What is claimed is:

1. A universal penetration test apparatus for measuring resistance of material to a challenge fluid, comprising:

an absorbent pad capable of absorbing the challenge fluid;

an elongated weight support assembly having a top end and a bottom end, the material being positionable between the pad and the elongated weight support assembly;

frame means for supporting the elongated weight support assembly in a vertical orientation;

a plurality of weight members being slidably receivable on the elongated weight support assembly, the elongated weight support assembly including flange means for supporting the weight members on the elongated weight support assembly;

the elongated weight assembly comprising a hollow sleeve and a rod, the sleeve being telescopically received on the rod, the rod including flange means for limiting movement of the sleeve along the rod, the sleeve including flange means for limiting movement of the weight members along the sleeve, the bottom end of the rod having concentric circles of varying widths cut at different depths with an inner most concentricity having the greatest depth.

2. A universal penetration test apparatus for measuring resistance of material to a challenge fluid, comprising:

an absorbent pad capable of absorbing the challenge fluid;

an elongated weight support assembly having a top end and a bottom end, the material being positionable between the pad and the elongated weight support assembly;

a weight member being slidably received by the elongated weight support assembly; and the elongated weight support assembly including a hollow sleeve and a rod, the sleeve being telescopically received on the rod, the rod including flange means for limiting movement of the sleeve along the rod, the sleeve including flange means for limiting movement of the weight member along the sleeve, the bottom end of the rod having concentric circles of varying widths cut at different depths with an inner most concentricity having the greatest depth.

3. A universal penetration test apparatus for measuring resistance of material to a challenge fluid, comprising:

an absorbent pad capable of absorbing the challenge fluid;

an elongated weight support assembly including a rod having a top end and a bottom end, the material being positionable between the pad and the bottom end of the rod, the bottom end of the rod having concentric circles of varying widths cut at different depths with an inner most concentricity having the greatest depth;

frame means for supporting the elongated weight support assembly in a vertical orientation; and at least one weight member being positionable on the elongated weight support assembly.

* * * * *